United States Patent [19]

Kolc et al.

[11] Patent Number: 4,913,900

[45] Date of Patent: Apr. 3, 1990

[54] CONDITIONING PERMANENT WAVE COMPOSITION AND METHOD

[75] Inventors: Stanley J. Kolc, Chicago; Gerald P. Newell, Hanover Park, both of Ill.

[73] Assignee: Helene Curtis, Inc., Chicago, Ill.

[21] Appl. No.: 200,614

[22] Filed: May 31, 1988

[51] Int. Cl.$^4$ .......................... A61K 7/09; A45D 7/04
[52] U.S. Cl. ...................................... 424/72; 132/204
[58] Field of Search ................. 424/72; 132/203, 204, 132/205

[56]  References Cited

U.S. PATENT DOCUMENTS

| 3,039,934 | 6/1962 | Whitmen et al. | 424/72 |
| 3,912,808 | 10/1975 | Sokol | 424/71 |
| 4,273,143 | 6/1981 | Klemm et al. | 424/71 X |
| 4,301,820 | 11/1981 | Cannell et al. | 132/204 |

Primary Examiner—Ellis P. Robinson
Assistant Examiner—Susan S. Rucker
Attorney, Agent, or Firm—Marshall, O'Toole, Gerstein, Murray & Bicknell

[57] ABSTRACT

A single formula, mild, alkaline permanent wave conditioning composition provides a strong, long lasting curl like an alkaline permanent wave composition but leaves the hair soft like an acid permanent wave composition while minimizing further damage to already damaged hair. The composition contains a water-soluble alkali salt of thioglycolic acid, such as ammonium thioglycolate in an amount of about 2% to about 22% by weight; a water-soluble alkaline dithiodiglycolate, such as diammonium dithiodiglycolate in an amount of about 0.1% to about 18% by weight; a hair softening and/or moisturizing agent, such as glycerine in an amount of about 0.1% to about 20% by weight; and sufficient additional alkali, if necessary, to bring the pH of the composition to about 7.5 to 8.7. This composition is easy to use and apply without damaging the hair while providing a strong, tight curl and leaving the hair unexpectedly soft. The composition can be lotion or water wrapped and can be used with or without heat. Unexpectedly, the composition is applied to any type of hair, regardless of structural damage to the hair, resulting in the same degree of curl tightness and softness.

22 Claims, No Drawings

CONDITIONING PERMANENT WAVE COMPOSITION AND METHOD

FIELD OF THE INVENTION

The present invention is directed to a composition and method for relatively permanently reshaping or curling human hair into a lasting curl pattern. More particularly, the present invention is directed to a composition and method capable of forming a "permanent" wave in human hair such that regardless of the condition of the hair, i.e., whether it be substantially undamaged or normal hair, tinted hair, frosted hair, bleached hair or hair substantially damaged as a result of some other prior hair treatment or environmental condition, the composition will permanently reshape both normal and damaged hair to substantially the same extent. The composition is applied to the hair as a single composition formula applied to both normal and damaged hair for the same period of time, with or without heating, as an alkaline wave composition to produce a strong curl like that of an alkaline permanent wave composition while leaving the hair feeling soft like an acid permanent wave composition.

BACKGROUND OF THE INVENTION AND PRIOR ART

In general, permanent waving of human hair is achieved by chemically breaking the sulfur to sulfur or disulfide cystine bonds occurring naturally in human hair and then reforming the cystine bonds while the hair is wrapped or curled on rods. The sulfur to sulfur cystine bonds in human hair maintain the hair in a naturally straight or curly configuration and, in order to permanently reshape the hair into a lasting, different configuration, a significant percentage of the sulfur to sulfur bonds must be broken and then reestablished after the hair is reconfigured in a desired position, such as wrapped around a suitable mandrel or roller. In general, the sulfur to sulfur cystine bonds are broken with a composition containing a reducing agent and after the hair is wound into a curl formation around a rod or roller, the sulfur to sulfur cystine bonds are relinked or reestablished while the hair is in the curl formation by contacting the hair in the new formation with an oxidizing agent, such as hydrogen peroxide or a water-soluble bromate.

There are three general types of permanent wave compositions or lotions used to break the cystine bonds in human hair, generally known as acid wave compositions; alkaline wave compositions; and neutral compositions. Of these three, the acid and alkaline wave compositions are most significant commercially. Permanent wave compositions containing an alkaline salt of thioglycolic acid (TG), such as ammonium thioglycolate as the reducing agent, are generally known as alkaline wave compositions and generally have a pH in the range of about 7.5 to about 9.4. The alkaline wave compositions are known as the conventional cold wave compositions, since free alkali penetrates and swells the hair shaft allowing the reducing agent to enter the hair shaft and break the sulfur to sulfur bonds without added heat. The permanent wave compositions containing glycerol monothioglycolate (GMTG) are known as acid wave compositions even though the pH of these compositions can be as as about 9.0. Generally speaking, the acid permanent wave compositions have a lower pH than the alkaline permanent wave compositions and, therefore, require heat and/or longer processing time to achieve sufficient reaction of the reducing agent. The alkaline permanent wave compositions produce a stronger, longer lasting curl while the acid permanent wave compositions provide a softer feel but a shorter curl duration.

The reducing action of mercaptans on keratin is due mostly to the dissociated form of the thiol groups, the thiolate anion. Acid permanent waves sufficiently curl hair at a lower pH compared to alkaline permanents because the waving agents in these permanents have low pKa values and thus exist predominantly in dissociated (thiolate) form at a pH near neutral, or slightly acidic pH. Hence, the pKa value shows that some mercaptans are efficient at high pH while others with a low pKa value and high ionization constant are efficient at lower pH values. For example, it is well known that the alkaline salts of thioglycolic acid, e.g., the ammonium salt of thioglycolic acid (pKa=10.4) has acceptable waving efficiency only if the pH of solution exceeds 9, see Zviak, Charles, The Science of Hair Care, Permanant Waving and Hair Straightening, p. 191, 1986; while amides such as thioglycolamide (pKa=8.4), and esters such as glycerol thioglycolate (pKa=7.8) give acceptable waving efficiency at neutral and even slightly acid pH.

The alkaline reducing agent combination of the composition and method of the present invention (thioglycolate and dithioglycolate) includes neither an amide reducing agent nor an ester reducing agent, yet is unexpectedly effective in the pH range of about 7.5 to 8.7 and particularly in the pH range of about 8.0 to 8.5.

Different reducing agents are effective to break the cystine bonds that crosslink human hair protein at different pH's. Generally speaking, the acid permanent wave compositions having a lower pH include reducing agents such as bisulfites, e.g., ammonium bisulfite, or glycerol monothioglycolate, capable of breaking the sulfur to sulfur cystine bonds within lower pH ranges, whereas the alkaline permanent wave compositions, having pH's in the range of about 7.5 to 9.5, require an alkaline salt of thioglycolic acid—so that the alkali can penetrate and swell the hair shaft for easier penetration of the reducing agent in order to break the sulfur to sulfur cystine bonds.

When the reducing agent is a salt of thioglycolic acid, such as ammonium thioglycolate, the reducing agent breaks the sulfur to sulfur cystine hair bonds best under high pH conditions (above 9.0) and therefore is included in a lotion in an amount sufficient to provide enough free alkali in solution for a composition pH of about 7.5 to 9.5. Alternatively, the high pH can be provided with a different alkali the reducing agent composition, such as a monoethanolamine, disopropanolamine or metal hydroxides. The lotion can be buffered, such as with ammonium bicarbonate or other known buffers, to maintain a suitable pH.

The use of diammonium dithioglycolate in acid or alkaline permanent lotions allows greater flexibility in processing time because it minimizes the possibility of overprocessing. This is due to the fact that the reaction of thioglycolic acid (TGA) with hair keratin is an equilibrium process. Thus by including diammonium dithiodiglycolate (oxidized TGA) in the wave lotion, the rate of the reaction of the thioglycolic acid with hair keratin is decreased and prevented from going to completion.

Generally, the permanent wave compositions of the prior art do not include moisturizers, such as glycerine, since moisturizers cause loss of curl, as disclosed in Cannell et al. U.S. Pat. No. 4,301,820.

One of the biggest problems associated with the permanent waving process is due to human error in the person applying the permanent waving lotion. If the reducing agent is applied to the hair shaft for the wrong period of time, too many or too few of the sulfur to sulfur bonds in the hair shaft are broken, resulting in seriously damaged hair or resulting in hair which has not been sufficiently treated to achieve a permanent wave with long lasting potential. Some of the reasons that the person applying the permanent wave composition has difficulty in determining the correct amount of time for processing is that the reducing agent reaction in breaking the sulfur to sulfur bonds is dependent upon the amount of heat applied to the hair; the amount of time the reducing agent is in contact with the hair; the concentration of reducing agent; the pH of the lotion applied; and the condition of hair.

Perhaps the most difficult factor for the applier of the permanent wave lotion to assess in determining how long to apply the reducing agent to the hair is the condition of the hair at the time of the permanent wave. It is well documented in the literature and prior art that the hair can be damaged by abuse of chemicals, e.g., by shampooing, permanent waving, tinting, frosting, bleaching, and particularly any hair treatment involving the use of hydrogen peroxide; mechanical treatment, e.g., thermal appliances; and environmental conditions, e.g., climate and pollution. It is well known that damaged hair, depending upon the stage and degree of damage of the hair, has significantly different chemical activity to reducing agents than normal or undamaged hair. If too many of the sulfur to sulfur bonds in the hair are broken by the reducing agent, the hair will be seriously weakened and may disintegrate.

It is theorized that somewhere in the range of about 20% to about 60% of the natural sulfur to sulfur cystine bonds in the hair shafts should be broken in order to give the hair the capability of being reshaped to any desired shape, such as curled around a rod or roller, and capable of retaining this shape. If too few of the sulfur to sulfur bonds are broken, the natural or normal configuration of the hair will predominate, causing the hair to retain its previous shape. This is because the predominant prior or natural bonds in the hair dictate that the hair will remain in the old configuration or shape. Hydrogen bonds are physically broken when wet hair is stretched and wrapped around a roller. When the hair is dried, the hydrogen bonds are reformed in a curled position or shape. While the hydrogen bonds aid to maintain the hair in the new configuration, the sulfur to sulfur cystine bonds are much stronger and, to a much greater extent than the hydrogen bonds, control the efficacy of the permanent wave.

In order to successfully provide a satisfactory permanent wave in the hair, the sulfur to sulfur cystine bonds reformed in the hair in the new or curled configuration, when the hair is later oxidized with the neutralizing agent, should be stronger than the prior or natural cystine hair bonds. It is desired, therefore, when permanent waving, that enough new bonds in a new hair configuration are formed during permanent waving to outweigh the number of old bonds remaining that tend to form the hair in its prior or natural configuration, whether it be straight or naturally curled.

Since damaged hair already has a significant number of the sulfur to sulfur cystine bonds broken due to some chemical, mechanical or environmental abuse, particularly the chemical abuses, such as bleaching, tinting or frosting, it is difficult to determine what length of time, and what reducing agent concentration to apply to the hair to provide the hair with the proper number of sulfur to sulfur bonds remaining after the reducing agent treatment. Significantly damaged hair, such as tinted hair, may require a reducing agent lotion application for a period of only about 5 minutes whereas a normal hair, not significantly damaged, may require the reducing agent lotion for a period of approximately 20 minutes under the same reducing agent concentration and temperature in order to result in both the damaged and normal hair having approximately the same curl configuration. Ideally, after the reducing agent treatment, every one of the hair shafts treated will contain the same ratio of broken to unbroken bonds so that this same ratio can be re-established in each hair shaft when the hair is in the new configuration to provide a consistent strong curl over the entire head of hair.

Generally, the reducing agent lotion is applied to the hair by first shampooing the hair and then applying the reducing agent lotion to the hair, either before or after the hair is wrapped around suitable rollers. Since it is not possible for even the experienced permanent wave applier to accurately determine visually the extent of damage to the hair in order to have a better idea of how long the reducing agent should be in contact with the hair, it is necessary to take a "test curl" so that after a predetermined amount of time, for example about 10 minutes, a first roller is removed from the hair and the curl is felt and stretched in an attempt to determine if the curl formation is strong enough. Once it is determined that the reducing agent has been in contact with the hair for a sufficient time period, the hair is rinsed thoroughly with water while still on the rollers or rods and, while the hair remains on the rollers or rods, a neutralizing agent is applied to oxidize and reform the sulfur to sulfur bonds while the hair is in the new, rolled configuration. The neutralizing agent contains an oxidizing agent, such as hydrogen peroxide or a bromate salt, in order to reestablish the sulfur to sulfur bonds to leave the hair in a relatively permanent, e.g., 2–4 months, new configuration. The neutralizing agent remains on the hair for approximately 5 to 10 minutes and then is rinsed thoroughly. The rods are removed, before or after rinsing out the neutralizing agent.

When the reducing agent lotion is applied to sections of the head prior to rolling that portion of the hair onto the rods it is called a lotion wrap whereas when the hair is rolled on the rods or rollers first and then the lotion applied onto all of the hair after rolling, this is called a water wrap. The timing for the reducing agent to be in contact with the hair for a lotion wrap is begun from the time that all rods are on the head, and the timing for a water wrap begins from the time that the lotion application is completed. The capability of using a water wrap is clearly more desirable since the lotion is applied to the entire head of hair all at once in a short period of time and can be rinsed from the hair all at once to provide a more uniform reducing agent contact time for all of the hair.

Relevant prior art patents directed to permanent waving compositions intended to permanently wave both normal and damaged hair are found in the Klemm et al U.S. Pat. No. 4,273,143; and Cannell et al U.S. Pat.

No. 4,301,820. Japanese patent No. 57-212110 appears to be directed to a post-permanent treatment containing glycerine to give hair sheen and luster.

In accordance with the present invention, an alkaline permanent wave composition is provided in a single formula which can be applied in a single predetermined amount of time to the hair, regardless of the structure of the hair, whether it be damaged or not, and this composition is capable of being water wrapped without the use of a dryer, hair caps or other heat treatment to speed the reducing agent reaction. The composition of the present invention produces a strong curl like an alkaline wave composition yet leaves the hair feeling soft like an acid wave composition.

Prior art compositions containing a salt of thioglycolic acid as a reducing agent are known to produce a tight curl but leave the hair feeling harsh due to the high alkalinity content. Prior art acid wave compositions containing glycerol monothioglycolate as a reducing agent require the mixing of the reducing agent into a separate lotion immediately prior to use since glycerol monothioglycolate will hydrolyze in contact with water and therefore must be kept separate until immediately prior to use. Further, the acid wave compositions generally require heat to help swell the hair for reaction with the reducing agent since the hair is not normally swelled sufficiently at the low pH of the acid wave compositions. The permanent wave compositions of the present invention solve the above-mentioned prior art deficiencies in both alkaline and acid permanent wave compositions.

SUMMARY OF THE INVENTION

In brief, the present invention is directed to a single formula, mild, alkaline permanent wave conditioning composition and method of permanently waving or re-shaping human hair that provides a strong, long lasting curl like an alkaline permanent wave composition but leaves the hair soft like an acid permanent wave composition while minimizing further damage to already damaged hair. Generally, the composition contains a water-soluble alkali salt of thioglycolic acid, such as ammonium thioglycolate in an amount of about 2% to about 22% by weight, preferably about 4% to about 16% by weight; a water-soluble alkaline dithiodiglycolate, such as diammonium dithiodiglycolate in an amount of about 0.1% to about 18% by weight, preferably about 0.1% to about 10% by weight; a hair softening and/or moisturizing agent, such as glycerine in an amount of about 0.1% to about 20% by weight, preferably about 0.1% to about 15% by weight; and sufficient additional alkali, if necessary, to bring the pH of the composition to about 7.5 to 8.7. This composition is easy to use and apply without damaging the hair while providing a strong, tight curl and leaving the hair unexpectedly soft. The composition can be lotion or water wrapped and can be used with or without heat. Unexpectedly, the composition is applied to any type of hair, regardless of structural damage to the hair, resulting in the same degree of curl tightness and softness.

Accordingly, an object of the present invention is to provide a new and improved permanent wave composition capable of breaking sulfur to sulfur bonds in human hair so that the hair can be reconfigured in a different configuration. The sulfur to sulfur human hair bonds can be reestablished with an oxidizing agent to maintain the new hair configuration for a substantial time period.

Another object of the present invention is to provide a new and improved permanent wave lotion containing a reducing agent capable of breaking sulfur to sulfur hair bonds without causing further significant damage to tinted, frosted, bleached or other substantially damaged hair.

Another object of the present invention is to provide a new and improved permanent wave lotion composition capable of breaking sulfur to sulfur human hair bonds leaving normal and damaged hair with approximately the same ratio of broken to unbroken sulfur to sulfur bonds when contacted with the composition for the same time period so that the same degree of curl tightness can be achieved in both normal and damaged hair.

Another object of the present invention is to provide a permanent wave composition including a hair softening and moisturizing agent that enhances the curl achieved with the composition.

These and other objects and advantages of the present invention will become apparent from the following detailed description of the preferred embodiment.

DETAILED DESCRIPTION OF THE PREFERRED EMBODIMENT

The present invention is directed to a permanent wave composition capable of permanently waving both damaged and undamaged hair in a single formulation, water-wrap, applied for a constant processing time as a mild alkaline permanent which unexpectedly leaves the hair feeling soft like an acid wave, yet produces a tight, long lasting curl formation similar to that of an alkaline wave. The capability of permanently waving both damaged and undamaged hair in a single formulation in a single processing time without requiring a test curl, without causing further damage to the hair, is totally unique in the industry and removes all room for error from the person applying the permanent wave lotion.

The composition of the present invention is a single formula, mild, alkaline permanent wave conditioning composition capable of waving or re-shaping human hair and provides a strong, long lasting curl like an alkaline permanent wave composition while leaving the hair soft like an acid permanent wave composition without further damaging already damaged hair. Generally, the composition contains a watersoluble alkaline salt of thioglycolic acid, such as ammonium thioglycolate in an amount of about 2% to about 22% by weight, particularly about 4% to about 16% by weight; a water-soluble alkaline dithiodiglycolate, such as diammonium dithiodiglycolate in an amount of about 0.1% to about 18% by weight particularly about 0.1% to about 10% by weight; and a hair moisturizer and/or softener selected from a polyhydroxyl alkyl compound, a polyalkylene glycol glycerol ether, an ethoxylated fatty alcohol, a fatty alcohol polymerized ether, and mixtures thereof in an amount of about 0.1% to about 20% by weight, particularly about 0.1% to about 15% by weight.

Optionally, the composition of the present invention includes a conditioner to improve the combing and manageability of the hair. Particularly, suitable conditioners are the polymeric quaternary ammonium salts, such as Polyquaternium 1 through Polyquaternium 14, inclusive, conditioners defined on page 245, CTFA Cosmetic Ingredient Dictionary, Third Edition, 1982, hereby incorporated by reference. The preferred conditioners are Polyquaternium-4, Polyquaternium-10 and Polyquaternium-11. The conditioner, when added, is included in an amount of about 0.01 to about 2.0% by weight of the composition.

Other common cosmetic additives can be incorporated into the composition of the present invention, as long as the basic properties of the permanent wave composition are not adversely affected. These additives include, but are not limited to, commonly used fragrances, dyes, opacifiers, pearlescing agents, thickeners, foam stabilizers, preservatives, water softening agents, acids, bases, buffers and the like; and will usually be present in weight percentages of less than about 1% each, and about 2% to about 5% in total. The composition vehicle is predominantly water but organic solvents also can be added to the composition in order to solubilize compounds that are not sufficiently soluble in water. Suitable solvents include the lower alcohols such as ethanol and isopropanol and mixtures. These solvents can be present in the hair setting composition of the present invention in an amount from about 1% to about 75% by weight and in particular from about 5% to about 50% by weight, based on the total weight of the composition.

The composition optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners such as bentonite. These thickeners, when included, preferably are present in an amount from about 0.1% to about 10% by weight and, in particular, from about 0.5% to about 3% by weight, based on the total weight of the composition.

In accordance with an important feature of the present invention, the moisturizer is capable of unexpectedly enhancing the curl formation achieved in accordance with the method of the present invention. The composition has a pH in the range of about 7.5 to 8.7. To achieve the full advantage of the present invention, the composition has a pH of about 8.0 to 8.5 for best curl retention when cold waved. This pH can be achieved by the addition of an alkanolamine, ammonia, an ammonium carbonate, or a metal hydroxide to the composition of the present invention.

In accordance with an important and unexpected feature of the present invention, it has been found that moisturizers actually enhance the curl formation when included in the permanent wave composition of the present invention. The use of polyhydric alcohols or polyhydroxy alkane compounds, such as ethylene glycol, glycerine, propylene glycol, or polyoxyethylene glyceryl ether in this composition leaves the hair in better condition due to humectant properties and surprisingly does not compromise curl formation, but provides the hair with a more uniform and natural curl.

These moisturizers are selected from the group consisting of polyhydroxyalkyl compounds, particularly alkylene glycols and polyalkylene glycols, and especially ethylene glycol and the polyethylene glycols; propylene glycol and the polypropylene glycols; polyethylene glycol glyceryl ethers; ethoxylated fatty alcohols; and fatty alcohol polyglycol ethers. Examples of suitable moisturizers include glycols and triols such as glycerine, ethylene glycol, propylene glycol,1,3-butylene glycol, 1,2,6-hexanetriol, 1,5-pentanediol, 2-methyl pentanediol-2,4, and 2-ethyl hexanediol-1,3. Further examples of suitable moisturizers include the polyalkylene glycols, such as those compounds having the formula

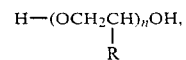

wherein R is H or $CH_3$, and n has an average value of 2 to 600; when R=H, particularly suitable moisturizers have n in the range of 4 to 600; and when R=$CH_3$, particularly suitable moisturizers have n in the range of 2 to 34. The polyalkylene glycols that can be used as moisturizers in the permanent wave composition of the present invention are exemplified by, but not limited to, compounds such as polyethylene glycol 200; polyethylene glycol 400; polyethylene glycol 600; polypropylene glycol 150; tetraethylene glycol; and dipropylene glycol.

Examples of other suitable moisturizers include the polyethylene glycol glyceryl ethers, such polyethylene glycol 600 glyceryl ether and polyethylene glycol 26 glyceryl ether. Furthermore, the ethoxylated nonyl phenols and ethoxylated octyl phenols, particularly nonoxynol, $C_9H_{19}C_6H_4(OCH_2CH_2)_n$—OH, wherein n averages at least 6 and up to about 100; and octoxynol, $C_8H_{17}C_6H_4(OCH_2CH_2)_n$—OH, wherein n averages at least 7 and up to about 40, also are suitable moisturizers for use in the composition of the present invention. Suitable ethoxylated fatty alcohols for use as moisturizers in the composition of the present invention include compounds having the formula R—$(OCH_2CH_2)_n$OH, wherein R is an alkyl group containing from about 12 to about 30 carbon atoms and n averages at least 6. In addition, fatty alcohol polyglycol ethers having the formula

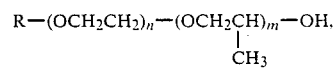

wherein R is an alkyl group containing from about 8 to about 18 carbon atoms, n=0 to 6, m=0 to 6, and n+m is at least 6, also are useful as moisturizers in the composition of the present invention.

The composition of the present invention is easy to use and apply without damaging the hair while providing a strong, tight curl and leaving the hair unexpectedly soft. The composition can be lotion or water wrapped and can be used with or without heat. Unexpectedly, the composition is applied to any type of hair, regardless of structural damage to the hair, resulting in the same degree of curl tightness and softness.

In the market today, alkaline permanent wave compositions fall into one of two categories. The first category, comprising about 90% of the alkaline permanent market, is alkaline permanents that require one lotion for normal hair and a different lotion for tinted hair: examples of compositions now being marketed that fall into this category are LUXURIANCE by Helene Curtis; DESIGN FREEDOM by Zotos and OPTI-FORM by Wella. The second category of alkaline permanents include a single lotion for both normal and tinted hair and comprises about 10% of the alkaline permanent market. Of the alkaline permanents that use a single lotion for both normal and tinted hair, every one requires a different process time for normal and tinted hair and the process time differs for each hair, depending upon the extent of damage, or requires a test curl to determine the amount of time necessary for processing, or requires the use of a dryer to fix the amount of processing time.

Examples of alkaline permanent compositions that require different process time for normal and tinted hair include CONTINUUM by Helene Curtis; HENNA by Helene Curtis; EURAWAV by Bonat; EXACTA by Matrix; and SCRUPLES by Professional Salon Products. Examples of those alkaline permanent wave compositions that require test curls include EXACTA by Matrix; EURAWAV by Bonat and SCRUPLES by Professional Salon Products. Examples of alkaline permanent wave compositions that require the use of a dryer to fix the processing time include CONTINUUM by Helene Curtis and SCRUPLES by Professional Salon Products.

It is most surprising in the art that the composition of the present invention is an alkaline permanent wave composition capable of treating both normal and damaged hair, particularly tinted hair and bleached hair, in a single formula, using a single, predetermined processing time for both normal and damaged hair and requires neither a test curl to determine the processing time nor a dryer to fix the processing time. Further surprising in accordance with the present invention is that the inclusion of a moisturizer, such as glycerine, within the alkaline permanent wave composition of the present invention actually enhances the springiness and permanency of the curl imparted by the alkaline permanent wave composition—exactly opposite to the prior art recognized problem of loss of curl when a softener of moisturizer is included within the alkaline permanent wave composition, such as disclosed in the Cannell et al U.S. Pat. No. 4,301,802.

The following Table I shows examples of leading alkaline and acid permanents in terms of wrapping, processing time and test curl and shows that the composition of the present invention is the only alkaline permanent capable of achieving permanent waving of both normal and damaged hair in a single processing time without a test curl while achieving the long lasting curl effects of an alkaline permanent:

TABLE I

| | # of Different Lotions | Type of Hair | Water or Lotion Wrap | Process Time | Test Curl |
|---|---|---|---|---|---|
| PRESENT INVENTION | 1 | Normal | Water | 20 Min. | No |
| | | Tinted | Water | 20 Min. | No |
| DESIGN FREEDOM (Alkaline) By: Zotos | 2 | Normal | Water | 20 Min. | No |
| | | Normal | Lotion | 10 Min. | No |
| | | Tinted | Water | 15 Min. | No |
| | | Tinted | Lotion | 5 Min. | Yes |
| EXACTA (Alkaline) By: Matrix | 1 | Normal | Water | 20 Min. | No |
| | | Tinted | Water | 5-10 Min. | Yes |
| | | Resistant | Water | 25-30 Min. | Yes |
| LUXURIANCE (Alkaline) By: Helene Curtis | 2 | Normal | Water | 20 Min. | No |
| | | Normal | Lotion | 10 Min. | No |
| | | Tinted | Water | 15 Min. | No |
| QUANTUM (Acid) By: Helene Curtis | 1 | Normal | Water | 20 Min. | No |
| | | Tinted | Water | 20 Min. | No |
| | | Frosted | Water | 20 Min. | No |
| QUANTUM EXTRA (Acid) By: Helene Curtis | 1 | Normal | Water | 20 Min. | No |
| | | Tinted | Water | 20 Min. | No |
| | | Hi Lift Tinted | Water | 15 Min. | No |
| POST | 1 | Normal | Water | 15 Min. | No |

TABLE I-continued

| | # of Different Lotions | Type of Hair | Water or Lotion Wrap | Process Time | Test Curl |
|---|---|---|---|---|---|
| IMPRESSIONS (Acid) By: Helene Curtis | | Tinted | Water | 10 Min. | No |
| | | Resistant | Water | 20 Min. | No |
| ACCLAIM (Acid) By: Zotos | 1 | Normal | Water | 25 Min. | No |
| | | Tinted | Water | 15 Min. | No |
| | | Hi Lift Tinted | Water | 10 Min. | Yes |
| | | Frosted | Water | Test Curl | Yes |

In salon testing of the composition of the present invention, hair stylists were asked why they liked the composition of the present invention after each experimental test permanent. Strong likes included the strong/firm/tight curls produced by the composition of the present invention; the fact that the composition did not dry out the hair but left the hair soft; the resulting curls were true-to-rod sized and the curls were bouncy and snappy. The capability of achieving a permanent wave leaving the hair soft while providing bouncy, snappy, strong, firm, tight curls is totally unexpected in the art of permanent waving and has heretofore been unachieved by prior art compositions.

TABLE I

| PREFERRED COMPOSITIONS | |
|---|---|
| Alkaline Thioglycolate Salt e.g. ammonium thioglycolate | 4–16% |
| Alkaline Dithioglycolate Salt e.g. diammonium dithioglycolate | 0.1–10% |
| Polyhydric alcohol e.g. glycerine, or a polyethylene glycol ether of a Polyhydric Alcohol e.g. a polyethylene glycol ether of glycerin, e.g. glycereth-26 | 0.1–15% |
| Polyquaternium 4, 10 or 11 | 0.01–2.0% |
| Nonoxyl | 0.1–2.0% |
| Water | q.s. to 100% |
| pH | 7.5 to 8.7 |

Obviously, many modifications and variations of the invention as hereinbefore set forth can be made without departing from the spirit and scope thereof and therefore only such limitations should be imposed as are indicated by the appended claims.

We claim:

1. A composition capable of breaking sulfur to sulfur bonds in human hair for permanently waving both damaged and undamaged hair in a single formulation and in a single processing time when in contact with said human air so that said hair can be reconfigured in a predetermined configuration, comprising an aqueous solution of an alkaline salt of thioglycolic acid in an amount of about 2% to about 22% by weight; an alkaline dithiodiglycolate in an amount of about 0.1% to about 18% by weight; a polyhydric moisturizing compound in an amount of about 0.1% to about 20% by weight, and sufficient alkali such that the composition has a pH of about 7.5 to 8.7.

2. The composition of claim 1 wherein the composition is capable of breaking 20% to 60% of the sulfur to sulfur bonds in substantially undamaged hair and significantly less sulfur to sulfur bonds in damaged hair when in contact with said hairs for substantially the same time period.

3. The composition of claim 1 wherein the polyhydric moisturizer is selected from the group consisting of polyhydroxyalkyl compounds; polyalkylene glycols; glyceryl ether compounds; ethoxylated fatty alcohols; ethoxylated alkyl phenols; and fatty alcohol polyglycol ether compounds; or mixtures thereof.

4. The composition of claim 1 wherein the alkaline salt of thioglycolic acid is included in an amount of about 4% to about 16% by weight of the composition; wherein the alkaline dithioglycolate is included in an amount of about 0.1% to about 10% by weight of the composition and wherein the moisturizing compound is included in an amount of about 0.1% to about 15% by weight of the composition.

5. The composition of claim 4 wherein the alkaline salt of thioglycolic acid is ammonium thioglycolate and wherein the alkaline dithioglycolate is diammonium dithioglycolate.

6. The composition of claim 1 wherein the moisturizer is a polyhydric alcohol or a polyalkylene glycol ether of a polyhydric alcohol.

7. The composition of claim 6 wherein the moisturizer is glycerine or a polyalkylene glycol ether of glycerine having an average ethoxylation value of 5 to 50.

8. The composition of claim 1 further including a polymeric quaternary ammonium compound in an amount of bout 0.1% to about 2.0% by weight of the composition.

9. The composition of claim 1 wherein the alkaline salt of thioglycolic acid is included in the composition in an amount of about 9% to about 16% by weight of the composition.

10. A method of breaking sulfur to sulfur bonds in human hair to leave the hair weakened so that it can be reconfigured to a predetermined configuration, while minimizing further damage to damaged hair, including contacting the hair for a predetermined amount of time with an aqueous reducing agent-containing composition comprising about 2% to about 22% by weight of an alkaline salt of thioglycolic acid; about 0.1% to about 18% of an alkaline dithiodiglycolate; about 0.1% to about 20% of a polyhydric moisturizing compound; and sufficient alkali such that the composition has a pH of 7.5 to 8.7; forming the hair in a desired configuration such that the hair is in contact with the reducing agent-containing composition for a predetermined amount of time while formed in the new configuration; and then removing most of the reducing agent-containing composition from the hair at the expiration of the predetermined time period.

11. The method of claim 10 further including wrapping a plurality of human hair sections around a plurality of mandrels to reconfigure the hair sections in a plurality of curl configurations such that the hair is curl-configured while in contact with the reducing agent-containing composition; and removing the mandrels sequentially after said predetermined time period without testing the hair from one of the first removed mandrels for curl tightness.

12. The method of claim 10 wherein the polyhydric moisturizer is selected from the group consisting of polyhydroxyalkyl compounds; polyalkylene glycols; glyceryl ether compounds; ,ethoxylated fatty alcohols; ethoxylated alkyl phenols; and fatty alcohol polyglycol ether compounds; or mixtures thereof.

13. The method of claim 10 wherein the alkaline salt of thioglycolic acid is included in an amount of about 4% to about 16% by weight of the composition; wherein the alkaline dithioglycolate is included in an amount of about 0.1% to about 10% by weight of the composition, and wherein the moisturizing compound is included in an amount of about 0.1% to about 15% by weight of the composition.

14. The method of claim 13 wherein the alkaline salt of thioglycolic acid is ammonium thioglycolate and wherein the alkaline dithioglycolate is diammonium dithioglycolate.

15. The method of claim 10 wherein the moisturizer is a polyhydric alcohol or a polyalkylene glycol ether of a polyhydric alcohol.

16. The method of claim 15 wherein the moisturizer is glycerine or a polyethylene glycol ether of glycerine having an average ethoxylation value of 5 to 50.

17. The method of claim 10 wherein the alkaline salt of thioglycolic acid is included in the composition in an amount of about 9% to about 16% by weight of the composition.

18. A method of treating two types of hair having substantially differing ratios of broken to unbroken disulfide bonds with a single formula of an alkaline permanent wave composition to achieve approximately the same ratio of broken to unbroken disulfide bonds in both types of hair comprising:

contacting the hair with a composition comprising a combination of reducing agents including an alkaline salt of thioglycolic acid and an alkaline dithioglycolate in an amount sufficient to break a sufficient number of disulfide hair bonds in both of the hair types such that upon oxidation of both types of hair, both types of hair will re-form into a different configuration; and a polyhydric moisturizer in an amount sufficient to enhance the permanency of the different configuration while softening the feel of the hair , said composition having a pH of about 7.5 to 8.7; and thereafter oxidizing both types of contacted hair, simultaneously, in the different configuration to re-form both damaged and undamaged hair types.

19. The method of claim 18 wherein after oxidation, both of the hair types have approximately the same ratio of broken to unbroken disulfide bonds.

20. The method of claim 18 wherein the alkaline salt of thioglycolic acid is included in an amount of about 4% to about 16% by weight of the composition; wherein the alkaline dithioglycolate is included in an amount of about 0.1% to about 10% by weight of the composition and wherein the moisturizing compound is included in an amount of about 0.1% to about 15% by weight of the composition.

21. The method of claim 18 wherein the polyhydric moisturizer is selected from the group consisting of polyhydroxyalkyl compounds; polyalkylene glycols; glyceryl ether compounds; ethoxylated fatty alcohols; ethoxylated alkyl phenols; and fatty alcohol polyglycol ether compounds; or mixtures thereof.

22. The method of claim 21 wherein the moisturizer is a polyhydric alcohol of the formula $$HOCH_2CHCH_2OH.$$
$$|$$
$$OH$$

a polyalkylene glycol either thereof, or mixtures thereof.

* * * * *